(12) United States Patent
Knapp et al.

(10) Patent No.: US 6,300,102 B1
(45) Date of Patent: Oct. 9, 2001

(54) **IMMUNOGENIC HYBRID PROTEIN OPRF-OPRL DERIVED FROM *PSEUDOMONAS AERUGINOSA* MEMBRANE PROTEINS**

(75) Inventors: Bernhard Knapp, Wetter; Klaus-Dieter Hungerer; Michael Bröker, both of Marburg; Bernd-Ulrich von Specht, Bahlingen/Kaiserstuhl; Horst Domdey, Neuried, all of (DE)

(73) Assignee: Chiron Behring GmbH & Co., Marburg (DE)

( * ) Notice: Subject to any disclaimer, the term of this patent is extended or adjusted under 35 U.S.C. 154(b) by 0 days.

(21) Appl. No.: 09/267,747

(22) Filed: Mar. 10, 1999

Related U.S. Application Data

(62) Division of application No. 08/572,447, filed on Dec. 14, 1995, now Pat. No. 5,955,090.

(30) Foreign Application Priority Data

Dec. 16, 1994 (EP) .................................................. 94120023

(51) Int. Cl.[7] .................................................... C12P 21/04

(52) U.S. Cl. .................... 435/69.7; 435/69.7; 435/320.1; 435/71.1; 435/71.2; 435/252.3; 536/23.7; 536/23.4; 424/260.1

(58) Field of Search ................................ 435/320.1, 69.1, 435/69.3, 71.1, 71.2, 440, 471, 252.3, 254.11, 257.2, 69.7, 69.8; 536/23.7, 23.1, 24.32, 23.4; 424/260.1, 192.1

(56) References Cited

U.S. PATENT DOCUMENTS 5,338,669 * 8/1994 Gillies .

FOREIGN PATENT DOCUMENTS

| 0 297 291 B1 | 1/1989 | (EP) . |
| 0 357 024 A2 | 3/1990 | (EP) . |
| WO 93/24636 | 12/1993 | (WO) . |
| 93/24636 * | 12/1993 | (WO) . |

OTHER PUBLICATIONS

GenCore Accession #M25761. Duchene et al., 1989.*
GenCore Accession #Q84578. Cornelis et al., 1995.*
GenCore Accession #N82023. Domedy et al., 1987.*
Duchene et al. J. Bacteriol. 170: 155–162, 1988.*
Martin et al. FEMS Microbiol. Lett. 113(3): 261–266, 1993.*
Duchene et al. J.Bacteriol. Aug. 1989. 171: 4130–4137, 1989.*
Baldari et al., "A Novel Leader Peptide Which Allows Efficient Secretion of a Fragment of Human Interleukin 1β in *Saccharomyces cerevisiae*,"*Embo J.* 6(1):229–234 (1987).

Duchene et al., "Sequence and Transcriptional Start Site of the *Pseudomonas aeruginosa* Outer Membrane Porin Protein F Gene," *J. Bacteriol.* 170(1):155–162 91988).
Duchene et al., "*Pseudomonas aeruginosa* Outer Membrane Viprotein I Gene: Molecular Cloning, Sequence, and Expression in *Escherichia coli*," *J. Bacteriol.* 171(8):4130–4137 (1989).
Finke et al., "Protection Against Experimental *Pseudomonas aeruginosa* Infection by Recombinant *P. aeruginosa* Lipoprotein I Expressed in *Escherichia coli* ," *Infect. Immun.* 58(7):2241–2244 (1990).
Finke et al., "Protection of Immunosuppressed Mice Against Infection With *Pseudomonas aeruginosa* by Recombinant *P. aeruginosa* Lipoprotein I and Lipoprotein I–Specific Monoclonal Antibodies," *Infect. Immun.* 59(4):1251–1254 (1991).
Finnen, Renee L., et al., "Anaylsis of the *Pseudomonas aeruginosa* Major Outer Membrane Protein OprF by Use of Truncated OprF Derivatives and Monoclonal Antibodies," *J. Bacteriol.* 174(15):4977–4985 (1992).
Horton et al., "Engineering Hybrid Genes Without the Use of Restriction Enzymes: Gene Splicing by Overlap Extension," *Gene* 77:61–68 (1989).
Hughes et al., "Synthetic Peptides Representing Epitopes of Outer Membrane Protein F of *Pseudomonas aeruginosa* That Elicit Antibodies Reactive With Whole Cells of Heterologous Immunotype Strains of *P. aeruginosa* that elicit Antibodies Reactive With Wholw Cells of Heterologous Immunotype Strains of *P. aeruginosa*," *Infec. Immun.* 60(9):3497–3503 (1992).
Johnson et al., "Improved Technique Utilizing Nonfat Dry Milk for Analysis of Proteins and Nucleic Acids Transferred to Nitrocellulose," *Gene Anal. Techn.* 1:3–8 (1984).
Roussilhon et al., "Responses of T Cells From Sensitized Donors to Recombinant and Synthetic Peptides corresponding to Sequences of the *Plasmodium falciparum* SERP Antigen," *Immunol. Lett.* 25:149–154 (1990).
Schorr et al., "Surface Expression of Malarial Antigens in *Salmonella typhimurium*: Induction of Serum Antibody Response Upon Oral Vaccination of Mice," *Vaccine* 9:675–681 (1991).
Von Specht et al., "Outer Membrane Proteins of *Pseudomonas aeruginosa* as Vaccine Candidates," *Behring Inst. Mitt.*, vol. 95:85–96.
European Patent Office Form 1503.

* cited by examiner

Primary Examiner—Jennifer E. Graser
(74) *Attorney, Agent, or Firm*—Roberta L. Robins; Alisa A. Harbin; Robert P. Blackburn

(57) ABSTRACT

The present invention relates to a hybrid protein comprising the *Pseudomonas aeruginosa* outer membrane protein I (OprI) which is fused with its amino terminal end to the carboxy-terminal end of a carboxy-terminal portion of the *Pseudomonas aeruginosa* outer membrane protein F (OprF), as well as to monoclonal or polyclonal antibodies against this hybrid protein. Both, the hybrid protein and the antibodies directed to the hybrid protein confer protection against an infection by *Pseudomonas aeruginosa* to laboratory animals or man.

9 Claims, 4 Drawing Sheets

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

AAAGAGCTCG CTCCGGCTCC GGAACCGGTT GCCGAC                36

(2) INFORMATION FOR SEQ ID NO:2:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

AAAAAGCTTA CTTGGCTTCG GCTTCTACTT CGG                    33

(2) INFORMATION FOR SEQ ID NO:3:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CGTACCATGG TGAGCAGCCA CTCCAAAGAA ACCGAAGCT              39

(2) INFORMATION FOR SEQ ID NO:4:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

AAAAAGCTTC TATTACTTGC GGCTGGCTTT TTCC                   34

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

TTCAACGCGA CGGTTGATAG CGCG                             24

(2) INFORMATION FOR SEQ ID NO:6:

(i) SEQUENCE CHARACTERISTICS:
        (A) LENGTH: 57 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GAAGGCCGCG CTATCAACCG TCGCGTTGAA AGCAGCCACT CCAAAGAAAC CGAAGCT        57

(2) INFORMATION FOR SEQ ID NO:7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

AAAGAGCTCC TTGCGGCTGG CTTTTTCAGC ATGCG        35

(2) INFORMATION FOR SEQ ID NO:8:

(i) SEQUENCE CHARACTERISTICS:
        (A) LENGTH: 192 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: YES (vi) ORIGINAL SOURCE:
        (A) ORGANISM: Pseudomonas aeruginosa
        (F) TISSUE TYPE: Serotype 6; ATCC 33354

(ix) FEATURE:
        (A) NAME/KEY: CDS
        (B) LOCATION:1..189
        (D) OTHER INFORMATION:/note= "Sequence is coding for oprI
            without signal sequence"

(xi) SEQUENCE DESCRIPTION: SEQ ID NO:8:

AGC AGC CAC TCC AAA GAA ACC GAA GCT CGT CTG ACC GCT ACC GAA GAC        48
Ser Ser His Ser Lys Glu Thr Glu Ala Arg Leu Thr Ala Thr Glu Asp
 1               5                  10                  15

GCA GCT GCT CGT GCT CAG GCT CGC GCT GAC GAA GCC TAT CGC AAG GCT        96
Ala Ala Ala Arg Ala Gln Ala Arg Ala Asp Glu Ala Tyr Arg Lys Ala
                20                  25                  30

GAC GAA GCT CTG GGC GCT GCT CAG AAA GCT CAG CAG ACC GCT GAC GAG       144
Asp Glu Ala Leu Gly Ala Ala Gln Lys Ala Gln Gln Thr Ala Asp Glu
            35                  40                  45

GCT AAC GAG CGT GCC CTG CGC ATG CTG GAA AAA GCC AGC CGC AAG           189
Ala Asn Glu Arg Ala Leu Arg Met Leu Glu Lys Ala Ser Arg Lys
    50                  55                  60

TAA                                                                   192

(2) INFORMATION FOR SEQ ID NO:9:

(i) SEQUENCE CHARACTERISTICS:
        (A) LENGTH: 63 amino acids
        (B) TYPE: amino acid
        (D) TOPOLOGY: linear (ii) MOLECULE TYPE: protein (xi) SEQUENCE DESCRIPTION: SEQ ID NO:9:

Ser Ser His Ser Lys Glu Thr Glu Ala Arg Leu Thr Ala Thr Glu Asp
1               5                   10                  15

Ala Ala Ala Arg Ala Gln Ala Arg Ala Asp Glu Ala Tyr Arg Lys Ala
            20                  25                  30

Asp Glu Ala Leu Gly Ala Ala Gln Lys Ala Gln Thr Ala Asp Glu
        35                  40                  45

Ala Asn Glu Arg Ala Leu Arg Met Leu Glu Lys Ala Ser Arg Lys
    50                  55                  60

(2) INFORMATION FOR SEQ ID NO:10:

(i) SEQUENCE CHARACTERISTICS:
      (A) LENGTH: 486 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: YES (vi) ORIGINAL SOURCE:
      (A) ORGANISM: Pseudomonas aeruginosa
      (F) TISSUE TYPE: Serotype 6; ATCC 33354

(ix) FEATURE:
      (A) NAME/KEY: CDS
      (B) LOCATION:1..483
      (D) OTHER INFORMATION:/note= "Sequence is coding for oprF
         C-terminus"

(xi) SEQUENCE DESCRIPTION: SEQ ID NO:10:

```
GCT CCG GCT CCG GAA CCG GTT GCC GAC GTT TGC TCC GAC TCC GAC AAC        48
Ala Pro Ala Pro Glu Pro Val Ala Asp Val Cys Ser Asp Ser Asp Asn
    65                  70                  75

GAC GGC GTC TGC GAC AAC GTC GAC AAG TGC CCG GAC ACC CCG GCC AAC        96
Asp Gly Val Cys Asp Asn Val Asp Lys Cys Pro Asp Thr Pro Ala Asn
 80                  85                  90                  95

GTC ACC GTT GAC GCC AAC GGC TGC CCG GCT GTC GCC GAA GTC GTA CGC       144
Val Thr Val Asp Ala Asn Gly Cys Pro Ala Val Ala Glu Val Val Arg
                100                 105                 110

GTA CAG CTG GAC GTG AAG TTC GAC TTC GAC AAG TCC AAG GTC AAA GAG       192
Val Gln Leu Asp Val Lys Phe Asp Phe Asp Lys Ser Lys Val Lys Glu
            115                 120                 125

AAC AGC TAC GCT GAC ATC AAG AAC CTG GCC GAC TTC ATG AAG CAG TAC       240
Asn Ser Tyr Ala Asp Ile Lys Asn Leu Ala Asp Phe Met Lys Gln Tyr
        130                 135                 140

CCG TCC ACT TCC ACC ACC GTT GAA GGT CAT ACC GAC TCC GTC GGT ACC       288
Pro Ser Thr Ser Thr Thr Val Glu Gly His Thr Asp Ser Val Gly Thr
    145                 150                 155

GAC GCT TAC AAC CAG AAG CTG TCC GAG CGT CGT GCC AAC GCC GTT CGT       336
Asp Ala Tyr Asn Gln Lys Leu Ser Glu Arg Arg Ala Asn Ala Val Arg
160                 165                 170                 175

GAC GTA CTG GTC AAC GAG TAC GGT GTG GAA GGT GGT CGC GTG AAC GCT       384
Asp Val Leu Val Asn Glu Tyr Gly Val Glu Gly Gly Arg Val Asn Ala
                180                 185                 190

GTC GGT TAC GGC GAG TCC CGC CCG GTT GCC GAC AAC GCC ACC GCT GAA       432
Val Gly Tyr Gly Glu Ser Arg Pro Val Ala Asp Asn Ala Thr Ala Glu
            195                 200                 205

GGC CGC GCT ATC AAC CGT CGC GTT GAA GCC GAA GTA GAA GCC GAA GCC       480
```

Gly Arg Ala Ile Asn Arg Arg Val Glu Ala Glu Val Glu Ala Glu Ala
        210                 215                 220

AAG TAA                                                                      486
Lys (2) INFORMATION FOR SEQ ID NO:11:

(i) SEQUENCE CHARACTERISTICS:
        (A) LENGTH: 161 amino acids
        (B) TYPE: amino acid
        (D) TOPOLOGY: linear (ii) MOLECULE TYPE: protein (xi) SEQUENCE DESCRIPTION: SEQ ID NO:11:

Ala Pro Ala Pro Glu Pro Val Ala Asp Val Cys Ser Asp Ser Asp Asn
  1               5                  10                  15

Asp Gly Val Cys Asp Asn Val Asp Lys Cys Pro Asp Thr Pro Ala Asn
                 20                  25                  30

Val Thr Val Asp Ala Asn Gly Cys Pro Ala Val Ala Glu Val Val Arg
             35                  40                  45

Val Gln Leu Asp Val Lys Phe Asp Phe Asp Lys Ser Lys Val Lys Glu
 50                  55                  60

Asn Ser Tyr Ala Asp Ile Lys Asn Leu Ala Asp Phe Met Lys Gln Tyr
 65                  70                  75                  80

Pro Ser Thr Ser Thr Thr Val Glu Gly His Thr Asp Ser Val Gly Thr
                 85                  90                  95

Asp Ala Tyr Asn Gln Lys Leu Ser Glu Arg Arg Ala Asn Ala Val Arg
                100                 105                 110

Asp Val Leu Val Asn Glu Tyr Gly Val Glu Gly Gly Arg Val Asn Ala
            115                 120                 125

Val Gly Tyr Gly Glu Ser Arg Pro Val Ala Asp Asn Ala Thr Ala Glu
        130                 135                 140

Gly Arg Ala Ile Asn Arg Arg Val Glu Ala Glu Val Glu Ala Glu Ala
145                 150                 155                 160

Lys (2) INFORMATION FOR SEQ ID NO:12:

(i) SEQUENCE CHARACTERISTICS:
        (A) LENGTH: 645 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: YES (vi) ORIGINAL SOURCE:
        (A) ORGANISM: Pseudomonas aeruginosa
        (F) TISSUE TYPE: Serotype 6; ATCC 33354

(ix) FEATURE:
        (A) NAME/KEY: CDS
        (B) LOCATION:1..642
        (D) OTHER INFORMATION:/note= "Sequence is coding for oprF
            C-terminus and oprI without signal sequence"

(xi) SEQUENCE DESCRIPTION: SEQ ID NO:12:

GCT CCG GAA CCG GTT GCC GAC GTT TGC TCC GAC TCC GAC AAC GAC GGC      48
Ala Pro Glu Pro Val Ala Asp Val Cys Ser Asp Ser Asp Asn Asp Gly

―continued

```
                    165                 170                 175
GTC TGC GAC AAC GTC GAC AAG TGC CCG GAC ACC CCG GCC AAC GTC ACC        96
Val Cys Asp Asn Val Asp Lys Cys Pro Asp Thr Pro Ala Asn Val Thr
            180                 185                 190

GTT GAC GCC AAC GGC TGC CCG GCT GTC GCC GAA GTC GTA CGC GTA CAG       144
Val Asp Ala Asn Gly Cys Pro Ala Val Ala Glu Val Val Arg Val Gln
            195                 200                 205

CTG GAC GTG AAG TTC GAC TTC GAC AAG TCC AAG GTC AAA GAG AAC AGC       192
Leu Asp Val Lys Phe Asp Phe Asp Lys Ser Lys Val Lys Glu Asn Ser
210                 215                 220                 225

TAC GCT GAC ATC AAG AAC CTG GCC GAC TTC ATG AAG CAG TAC CCG TCC       240
Tyr Ala Asp Ile Lys Asn Leu Ala Asp Phe Met Lys Gln Tyr Pro Ser
                230                 235                 240

ACT TCC ACC ACC GTT GAA GGT CAT ACC GAC TCC GTC GGT ACC GAC GCT       288
Thr Ser Thr Thr Val Glu Gly His Thr Asp Ser Val Gly Thr Asp Ala
                245                 250                 255

TAC AAC CAG AAG CTG TCC GAG CGT CGT GCC AAC GCC GTT CGT GAC GTA       336
Tyr Asn Gln Lys Leu Ser Glu Arg Arg Ala Asn Ala Val Arg Asp Val
                260                 265                 270

CTG GTC AAC GAG TAC GGT GTG GAA GGT GGT CGC GTG AAC GCT GTC GGT       384
Leu Val Asn Glu Tyr Gly Val Glu Gly Gly Arg Val Asn Ala Val Gly
            275                 280                 285

TAC GGC GAG TCC CGC CCG GTT GCC GAC AAC GCC ACC GCT GAA GGC CGC       432
Tyr Gly Glu Ser Arg Pro Val Ala Asp Asn Ala Thr Ala Glu Gly Arg
290                 295                 300                 305

GCT ATC AAC CGT CGC GTT GAA AGC AGC CAC TCC AAA GAA ACC GAA GCT       480
Ala Ile Asn Arg Arg Val Glu Ser Ser His Ser Lys Glu Thr Glu Ala
                310                 315                 320

CGT CTG ACC GCT ACC GAA GAC GCA GCT GCT CGT GCT CAG GCT CGC GCT       528
Arg Leu Thr Ala Thr Glu Asp Ala Ala Ala Arg Ala Gln Ala Arg Ala
                325                 330                 335

GAC GAA GCC TAT CGC AAG GCT GAC GAA GCT CTG GGC GCT GCT CAG AAA       576
Asp Glu Ala Tyr Arg Lys Ala Asp Glu Ala Leu Gly Ala Ala Gln Lys
                340                 345                 350

GCT CAG CAG ACC GCT GAC GAG GCT AAC GAG CGT GCC CTG CGC ATG CTG       624
Ala Gln Gln Thr Ala Asp Glu Ala Asn Glu Arg Ala Leu Arg Met Leu
        355                 360                 365

GAA AAA GCC AGC CGC AAG TAA                                           645
Glu Lys Ala Ser Arg Lys
370                 375
```

(2) INFORMATION FOR SEQ ID NO:13:

(i) SEQUENCE CHARACTERISTICS:
        (A) LENGTH: 214 amino acids
        (B) TYPE: amino acid
        (D) TOPOLOGY: linear (ii) MOLECULE TYPE: protein (xi) SEQUENCE DESCRIPTION: SEQ ID NO:13:

```
Ala Pro Glu Pro Val Ala Asp Val Cys Ser Asp Ser Asp Asn Asp Gly
1               5                   10                  15

Val Cys Asp Asn Val Asp Lys Cys Pro Asp Thr Pro Ala Asn Val Thr
            20                  25                  30

Val Asp Ala Asn Gly Cys Pro Ala Val Ala Glu Val Val Arg Val Gln
        35                  40                  45

Leu Asp Val Lys Phe Asp Phe Asp Lys Ser Lys Val Lys Glu Asn Ser
    50                  55                  60

Tyr Ala Asp Ile Lys Asn Leu Ala Asp Phe Met Lys Gln Tyr Pro Ser
```

```
                 65                  70                  75                  80
Thr Ser Thr Thr Val Glu Gly His Thr Asp Ser Val Gly Thr Asp Ala
                         85                  90                  95
Tyr Asn Gln Lys Leu Ser Glu Arg Arg Ala Asn Ala Val Arg Asp Val
                100                 105                 110
Leu Val Asn Glu Tyr Gly Val Glu Gly Gly Arg Val Asn Ala Val Gly
            115                 120                 125
Tyr Gly Glu Ser Arg Pro Val Ala Asp Asn Ala Thr Ala Glu Gly Arg
    130                 135                 140
Ala Ile Asn Arg Arg Val Glu Ser Ser His Ser Lys Glu Thr Glu Ala
145                 150                 155                 160
Arg Leu Thr Ala Thr Glu Asp Ala Ala Arg Ala Gln Ala Arg Ala
                165                 170                 175
Asp Glu Ala Tyr Arg Lys Ala Asp Glu Ala Leu Gly Ala Ala Gln Lys
                180                 185                 190
Ala Gln Gln Thr Ala Asp Glu Ala Asn Glu Arg Ala Leu Arg Met Leu
            195                 200                 205
Glu Lys Ala Ser Arg Lys
    210
```

(2) INFORMATION FOR SEQ ID NO:14:

(i) SEQUENCE CHARACTERISTICS:
        (A) LENGTH: 681 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: YES (vi) ORIGINAL SOURCE:
        (A) ORGANISM: Pseudomonas aeruginosa
        (F) TISSUE TYPE: Serotype 6; ATCC 33354

(ix) FEATURE:
        (A) NAME/KEY: CDS
        (B) LOCATION:1..678
        (D) OTHER INFORMATION:/note= "Sequence is coding for oprI
           without signal sequence and oprF C-terminus"

(xi) SEQUENCE DESCRIPTION: SEQ ID NO:14:

```
AGC AGC CAC TCC AAA GAA ACC GAA GCT CGT CTG ACC GCT ACC GAA GAC        48
Ser Ser His Ser Lys Glu Thr Glu Ala Arg Leu Thr Ala Thr Glu Asp
215                 220                 225                 230

GCA GCT GCT CGT GCT CAG GCT CGC GCT GAC GAA GCC TAT CGC AAG GCT        96
Ala Ala Ala Arg Ala Gln Ala Arg Ala Asp Glu Ala Tyr Arg Lys Ala
                235                 240                 245

GAC GAA GCT CTG GGC GCT GCT CAG AAA GCT CAG CAG ACC GCT GAC GAG       144
Asp Glu Ala Leu Gly Ala Ala Gln Lys Ala Gln Gln Thr Ala Asp Glu
            250                 255                 260

GCT AAC GAG CGT GCC CTG CGC ATG CTG GAA AAA GCC AGC CGC AAG GAG       192
Ala Asn Glu Arg Ala Leu Arg Met Leu Glu Lys Ala Ser Arg Lys Glu
            265                 270                 275

CTC GCT CCG GCT CCG GAA CCG GTT GCC GAC GTT TGC TCC GAC TCC GAC       240
Leu Ala Pro Ala Pro Glu Pro Val Ala Asp Val Cys Ser Asp Ser Asp
        280                 285                 290

AAC GAC GGC GTC TGC GAC AAC GTC GAC AAG TGC CCG GAC ACC CCG GCC       288
Asn Asp Gly Val Cys Asp Asn Val Asp Lys Cys Pro Asp Thr Pro Ala
295                 300                 305                 310
```

```
AAC GTC ACC GTT GAC GCC AAC GGC TGC CCG GCT GTC GCC GAA GTC GTA    336
Asn Val Thr Val Asp Ala Asn Gly Cys Pro Ala Val Ala Glu Val Val
            315                 320                 325

CGC GTA CAG CTG GAC GTG AAG TTC GAC TTC GAC AAG TCC AAG GTC AAA    384
Arg Val Gln Leu Asp Val Lys Phe Asp Phe Asp Lys Ser Lys Val Lys
            330                 335                 340

GAG AAC AGC TAC GCT GAC ATC AAG AAC CTG GCC GAC TTC ATG AAG CAG    432
Glu Asn Ser Tyr Ala Asp Ile Lys Asn Leu Ala Asp Phe Met Lys Gln
            345                 350                 355

TAC CCG TCC ACT TCC ACC ACC GTT GAA GGT CAT ACC GAC TCC GTC GGT    480
Tyr Pro Ser Thr Ser Thr Thr Val Glu Gly His Thr Asp Ser Val Gly
        360                 365                 370

ACC GAC GCT TAC AAC CAG AAG CTG TCC GAG CGT CGT GCC AAC GCC GTT    528
Thr Asp Ala Tyr Asn Gln Lys Leu Ser Glu Arg Arg Ala Asn Ala Val
375                 380                 385                 390

CGT GAC GTA CTG GTC AAC GAG TAC GGT GTG GAA GGT GGT CGC GTG AAC    576
Arg Asp Val Leu Val Asn Glu Tyr Gly Val Glu Gly Gly Arg Val Asn
                395                 400                 405

GCT GTC GGT TAC GGC GAG TCC CGC CCG GTT GCC GAC AAC GCC ACC GCT    624
Ala Val Gly Tyr Gly Glu Ser Arg Pro Val Ala Asp Asn Ala Thr Ala
            410                 415                 420

GAA GGC CGC GCT ATC AAC CGT CGC GTT GAA GCC GAA GTA GAA GCC GAA    672
Glu Gly Arg Ala Ile Asn Arg Arg Val Glu Ala Glu Val Glu Ala Glu
            425                 430                 435

GCC AAG TAA                                                        681
Ala Lys
    440

(2) INFORMATION FOR SEQ ID NO:15:

(i) SEQUENCE CHARACTERISTICS:
        (A) LENGTH: 226 amino acids
        (B) TYPE: amino acid
        (D) TOPOLOGY: linear (ii) MOLECULE TYPE: protein (xi) SEQUENCE DESCRIPTION: SEQ ID NO:15:

Ser Ser His Ser Lys Glu Thr Glu Ala Arg Leu Thr Ala Thr Glu Asp
1               5                   10                  15

Ala Ala Ala Arg Ala Gln Ala Arg Ala Asp Glu Ala Tyr Arg Lys Ala
            20                  25                  30

Asp Glu Ala Leu Gly Ala Ala Gln Lys Ala Gln Thr Ala Asp Glu
        35                  40                  45

Ala Asn Glu Arg Ala Leu Arg Met Leu Glu Lys Ala Ser Arg Lys Glu
    50                  55                  60

Leu Ala Pro Ala Pro Glu Pro Val Ala Asp Val Cys Ser Asp Ser Asp
65                  70                  75                  80

Asn Asp Gly Val Cys Asp Asn Val Asp Lys Cys Pro Asp Thr Pro Ala
            85                  90                  95

Asn Val Thr Val Asp Ala Asn Gly Cys Pro Ala Val Ala Glu Val Val
            100                 105                 110

Arg Val Gln Leu Asp Val Lys Phe Asp Phe Asp Lys Ser Lys Val Lys
            115                 120                 125

Glu Asn Ser Tyr Ala Asp Ile Lys Asn Leu Ala Asp Phe Met Lys Gln
            130                 135                 140

Tyr Pro Ser Thr Ser Thr Thr Val Glu Gly His Thr Asp Ser Val Gly
145                 150                 155                 160
```

-continued

```
Thr Asp Ala Tyr Asn Gln Lys Leu Ser Glu Arg Arg Ala Asn Ala Val
                165                 170                 175

Arg Asp Val Leu Val Asn Glu Tyr Gly Val Glu Gly Gly Arg Val Asn
                180                 185                 190

Ala Val Gly Tyr Gly Glu Ser Arg Pro Val Ala Asp Asn Ala Thr Ala
            195                 200                 205

Glu Gly Arg Ala Ile Asn Arg Arg Val Glu Ala Glu Val Glu Ala Glu
    210                 215                 220

Ala Lys
225
```

IMMUNOGENIC HYBRID PROTEIN OPRF-OPRL DERIVED FROM *PSEUDOMONAS AERUGINOSA* MEMBRANE PROTEINS

This is a divisional of application Ser. No. 08/572,447, filed Dec. 14, 1995, issued Sep. 21, 1999 as U.S. Pat. No. 5,955,090, from which priority is claimed pursuant to 35 U.S.C. §120, which application in turn claims priority under 35 U.S.C. §119 to European Patent Application No. P 94120023.0, filed Dec. 16, 1994.

FIELD OF THE INVENTION

The present invention relates to a hybrid protein comprising the *Pseudomonas aeruginosa* outer membrane protein I (OprI or OMPI) which is fused with its amino terminal end to the carboxy-terminal end of a carboxy-terminal portion of the *Pseudomonas aeruginosa* outer membrane protein F (OprF or OMPF), as well as to monoclonal or polyclonal antibodies against this hybrid protein. Both, the hybrid protein and the antibodies directed to the hybrid protein confer protection against an infection by *Pseudomonas aeruginosa* to laboratory animals or man.

BACKGROUND OF THE INVENTION

*Pseudomonas aeruginosa* is an opportunistic gram-negative pathogen. It represents a major course of hospital-aquired infections, especially in burnt and other immuno-compromised patients, including transplant or cancer patients. Therefore, it is regarded as a "problem microbe" in human medicine.

Many efforts have been made so far in order to develop a vaccine against *Pseudomonas aeruginosa*. For example, in the EP-0 297 291 the complete amino acid-sequence of the outer membrane protein F, as well as the nucleotide sequence coding for OprF is disclosed. In the EP-0 357 024 the complete amino acid sequence of the outer membrane protein I and, additionally, the nucleotide sequence coding for OprI is shown. Furthermore, with both proteins it was shown that they may be useful for conferring immunoprotection against Pseudomonas aeruginosa to an animal or human proband. However, improvement of procedures of vaccination against a lethal *Pseudomonas aeruginosa* infection is still an object.

SUMMARY OF THE INVENTION

Surprisingly, it was found by the inventors that a hybrid protein, wherein OprI is linked with its N-terminal end to a C-terminal portion of OprF is significantly more immunogenic than fusion proteins only comprising OprI or OprF or mixtures of the latter fusion proteins.

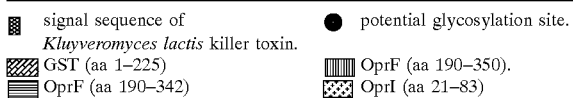

- signal sequence of *Kluyveromyces lactis* killer toxin.
- GST (aa 1–225)
- OprF (aa 190–342)
- potential glycosylation site.
- OprF (aa 190–350).
- OprI (aa 21–83)

Figure 2:
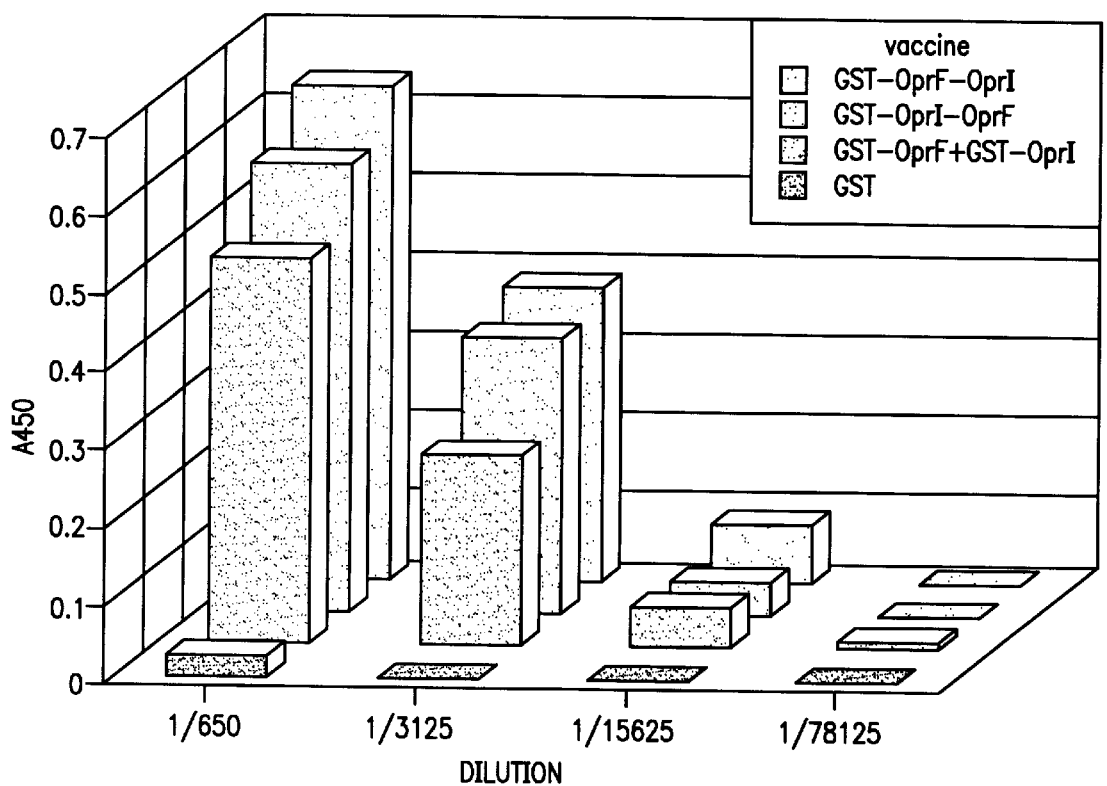

FIG. 2 is a determination of antibody titers against *P. aeruginosa* in sera of mice immunized with the indicated GST linked recombinant outer membrane vaccine or with GST alone. ELISA measurements were carried out on plates coated with sonicated *P. aeruginosa* serogroup 12.

Figure 3:
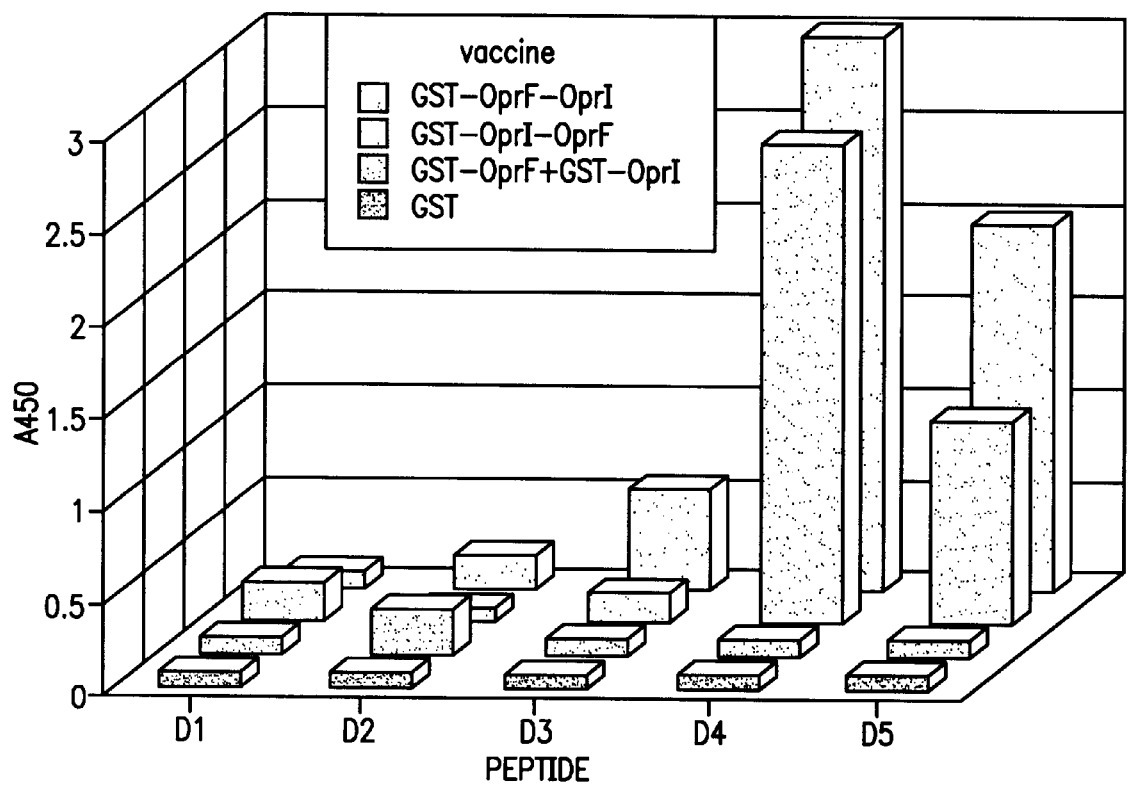

FIG. 3 is an antibody determination by ELISA against synthetic peptides D1–D5 listed in Table 1, which represent B-cell epitopes of OprF. Mice were immunized four times with the indicated recombinant fusion proteins or GST alone.

Figure 4:
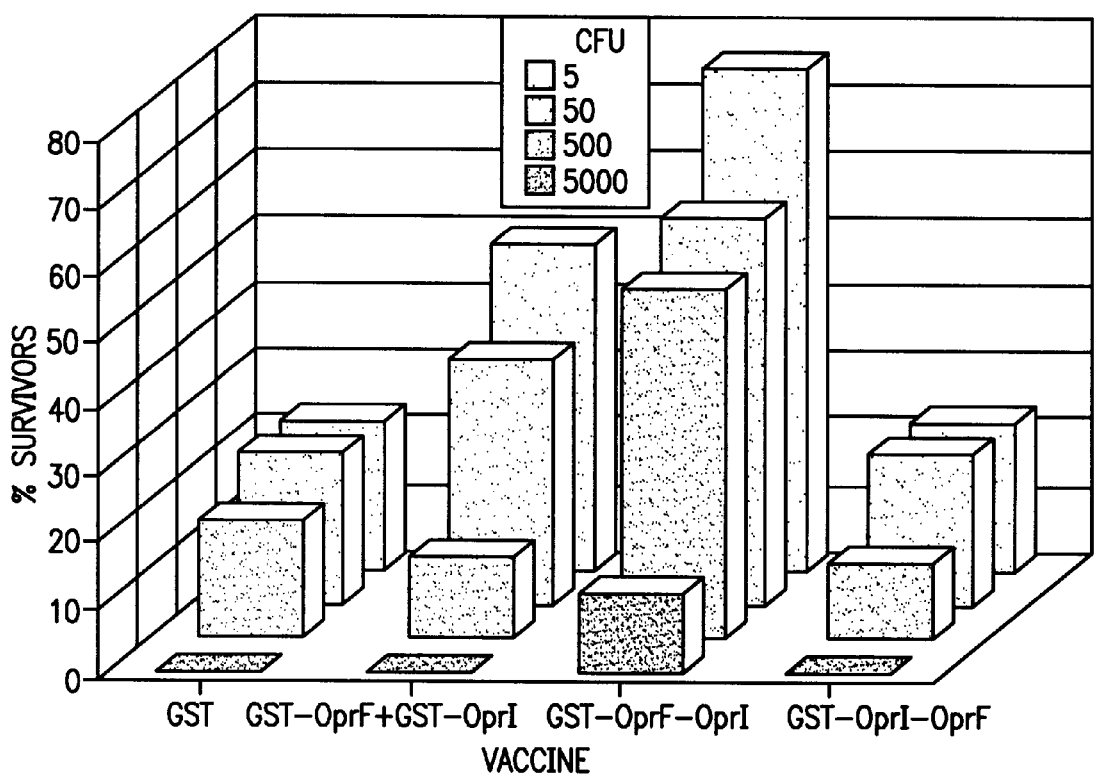

FIG. 4 demonstrates survival of BALB/c mice after immunization with the indicated vaccine or GST alone, followed by immunosuppression and intraperitoneal challenge with 5, 50, 500 or 5000 colony forming units of *P. aeruginosa* serogroup 1. Bars represent percentage of survivors (n=16–17) per challenge dose.

DETAILED DESCRIPTION OF THE INVENTION

Thus, the present invention relates to a hybrid protein comprising the *Pseudomonas aeruginosa* outer membrane protein I which is fused with its amino-terminal end to the carboxy-terminal end of a carboxy-terminal portion of the *Pseudomonas aeruginosa* outer membrane protein F, said carboxy-terminal portion comprising the sequence from aa 190 to aa 350. In a preferred embodiment said carboxy terminal portion is the sequence from aa 190 to aa 342.

The present invention further relates to a hybrid protein comprising the *Pseudomonas aeruginosa* outer membrane protein I which is fused with its amino terminal end to the carboxy-terminal end of a carboxy-terminal portion of the *Pseudomonas aeruginosa* outer membrane protein OprF, wherein said carboxy-terminal portion comprises one or more of the surface-exposed B-cell epitopes SEE.1, SEE 2, SEE 3and SEE 4. These B-cell epitopes are located at the following amino acid (aa) positions of the OprF: SEE 1=aa 212–240, SEE 2=aa 243–256, SEE 3=aa 285–298 and SEE 4=aa 332–350 (see example 1 and Hughes et al. (1992), Infect. Immun. 60, pp. 3497–3503).

Another embodiment of the present invention is a vaccine comprising at least one of the above-mentioned hybrid proteins.

Moreover, the present invention relates to monoclonal or polyclonal antibodies directed to one or more of the above hybrid proteins. These antibodies may also be used in a vaccine in order to confer passive protection against an infection by *Pseudomonas aeruginosa* to a subject.

Further aspects of the present invention are nucleic acids which are coding for the above-mentioned hybrid proteins.

Additionally, the present invention relates to a process for the preparation of the above-mentioned hybrid proteins, which comprises bringing about the expression of a nucleic acid as mentioned above, which is coding for a hybrid protein according to the invention, in pro- or eukaryotic cells.

The invention is further explained in detail in the examples which follow and in the claims.

In the following the sources of the microorganisms and the DNAs as well as methods that were used in the following examples, and which are for example regarded useful for carrying out the invention are indicated.

Microorganisms: *P. aeruginosa* International Antigenic Typing Scheme serogroup I (ATCC 33348) was obtained from A Bauernfeind, Max. von PettenkoferInstitut, University of Munich. Bacteria were grown and adjusted to the required concentration as previously described (Finke, M. et al. (1990), Infect. Immun., 58, pp. 2241–2244). For the expression of recombinant proteins *E. coli* K-12 W3110 lacI$^Q$L8 was used. For expression of OPRs in yeast we used Saccharomyces cerevisiae strain HT393 (leu2, ura3 pra1, prb1, prc1, pre1, cps1).

Source of DNAs: Three recombinant plasmids were used as the source of DNAs: pFSauI, a pUC19 derived plasmid that contains a 1,0 kb Sau 3Al-fragment of the *P. aeruginosa* outer membrane protein F gene encoding the C-terminal part of the protein from amino acid positions 57 to 350 (Duchene, M. et al. (1988), J. Bacteriol. 170, pp. 155–162); (SEQ ID NOs:10 and 11) pIIaq1, a pUC19 derived plasmid that contains a 626 bp TaqI-fragment spanning the complete OprI gene (Duchêne, M. et al. (1989), J. Bacteriol. 171, pp. 4130–4137),(SEQ ID NOs:8 and 9) and the expression vector pGEX-2a originating from the vector pGEX-2T modified by the introduction of the polylinker from vector pTRC. The vector pGEX-2a contains the tac promoter followed by the coding sequence for 26 kDa Schistosoma japonicum glutathione-S-transferase, a cleavage site for thrombin and the pTRC specific polyylinker region.

Characterization of antisera induced against synthetic peptides: Synthetic peptides representing amino acid regions 190–213 (D1), 212–240 (D2, SEE 1), 239–250 (D3), 284–316 (D4), and 332–350 (D5, SEE 4) from OprF were synthesized as described in (Roussilhon, C. E. et al. (1990) Immunol. Lett. 25, pp. 149–154)., Rabbits were immunized subcutaneously at eight different locations near lymph nodes with 200 µg KLH conjugated peptide in complete Freund's adjuvant, and reimmunized two weeks later with 400 µg of the conjugate in incomplete Freund's adjuvant. The animals received two booster injections intravenously of 150 µg and 100 µg of conjugate six and nine weeks after the first immunization. Antibody titers against peptides were measured by ELISA on plates coated with 5 ng per ml of peptide solution in 50 mM sodium phosphate buffer, pH 7.5 (PBS) overnight at room temperature. Plates were washed three times with 0.05 M citric acid and 0.05 M Tris, pH 7.4, and then dried over silica gel for 3 days. Rabbit sera were diluted 1:160 and saturated with *E. coli* proteins. Western blot analysis with recombinant. GST fusion-proteins and immunofluorescence determinations against intact *P. aeruginosa* serogroup 11 (ATCC 33.358) were carried out by a method reported in the literature (Johnson, D. A. et al. (1984) Gene Anal. Techn. 1, p. 3–8), Schnorr, J. B. et al. (1991), Vaccine 9, pp. 675–681).

Expression of OprF and OprI as glutathion-S-transferase fusion proteins: The oligonucleotides p1 (5'-AAA GAG CTC GCT CCG GCT CCG GAA CCG GTT GCC GAC-3') (SEQ ID NO:1) with a SacI restriction site at the 5' end, corresponding to bases 568 to 594 of the OprF gene, and p2, (5'-AAA AAG CTT ACT TGG CTT CGG CTT CTA CTT CGG-3') (SEQ ID NO:2) with a HindIII restriction site at the 5' end, complementary to bases 1028 to 1053 of the OprF gene, and 10 ng of the plasmid pFSauI were employed for a polymerase chain reaction, using the Perkin Elmer Cetus Gen-Amp Kit, which yielded a 500 bp fragment. The amplified fragment was digested with SacI and HindIII and introduced into the vector pGEX-2a to obtain plasmid pGEX-OprF (SEQ ID NO:10), which encodes the C-terminal part of the porin OprF from amino acids 190 to 350 (SEQ ID NO:11). The-oligonucleotides p3 (5'-CGT ACC ATG GTG AGC AGC CAC TCC AAA GAA ACC GAA GCT-3'), (SEQ ID NO:3) with an NcoI restriction site at the 5' end corresponding to bases 61 to 87 of the coding region of the OprI gene, and p4 (5'-AAA AAG CTT CTA TTA CTT GCG GCT GGC TTT TTC C-3'), SEQ ID NO:4) with a HindIII restriction site at the 5' end complementary to bases 231 to 255 of the coding region of the OprI gene, and 10 ng of the plasmid DNA pITaq1 were used in a polymerase chain reaction to amplify a 215 bp fragment, which was then treated with the restriction enzymes NcoI and HindIII to introduce it into the corresponding sites of the expression vector pGEX-2a, in order to obtain plasmid pGEX-OprI (SEQ ID NO:8), which encodes amino acids 21 to 83 of OprI (SEQ ID NO:9).

Construction of the GST-OprI-OprF and GST-OprF-OprI hybrid genes: The oligonucleotides p1 (see above) and p5 (5'-TTC AAC GCG ACG GTT GAT AGC GCG-3') (SEQ ID NO:5)(which is complementary to bases 1003 to 1026 of the OprF gene) and 10 ng of the plasmid pFSau1 were used to amplify a 470 bp QprF fragment. A second polymerase chain reaction was carried out with 10 ng of plasmid pITaq1 and the oligonucleotides p4 (see above) and p6 (5'-GAA GGC CGC GCT ATC AAC CGT CGC GTT GAA AGC AGC CAC TCC AAA GAA ACC GAA GCT-3'), (SEQ ID NO:6) in which nucleotides 1 through 30 correspond to bases 997 to 1026 of the OprF gene and nucleotides 31 through 57 correspond to bases 61 through 87 of the OprI coding region. This yielded a 240 bp fragment. 150 ng of both obtained DNA fragments and oligonucleotides p1 and p4 were used for a third polymerase chain reaction as described by Horton (Horton, R. M. et al. (1989), Gene 77, pp. 61–68); The obtained 660 bp fragment was digested with the restriction endonucleases SacI and HindIII, and introduced into the vector pGEX-2a to obtain plasmid pGEX-OprF-OprI, which encodes amino acids 190 to 342 of OprF (SEQ ID NOs:12 and 13) and amino acids 21 to 83 of OprI. The oligonucleotides p3 and p7 (5'-AAA GAG CTC CTT GCG GCT GGC TTT TT CAG CAT GCG-3') (SEQ ID NO:7) with a SacI restriction site at the 5' end, complementary to bases 223 to 249 of the coding region from the OprI gene, and 10 ng of plasmid pITaq1 were used to amplify a 210 bp fragment, which was intruduced into the vector pGEX2a with the help of the restriction enzymes NcoI and SAcI. The obtained plasmid was digested with the enzymes SacI and HindIII to introduce a 490 bp fragment obtained by digestion of the plasmid pGEX-OprF, using the corresponding enzymes. Plasmid pGEX-OprI-OprF (SEQ ID NOs:14 and 15) encodes amino acids 21 to 83 from OprI and amino acids 190 to 350 from OprF, which are separated by a two amino acid linker introduced at the SacI cloning site.

Expression and purification of the recombinant proteins in *E. coli:* The four plasmids pGEX-OprF, pGEX-OprI, pGEX-OprF-OprI and pGEX-OprI-OprF were transformed into the *E. coli* K-12 strain W3110 lac I$^Q$L8. For large scale antigen production, 5-liter bacterial cultures containing the plasmids were left to grow to $OD_{660}$=1 and the expression of the *P. aeruginosa* specific recombinant antigens induced by isopropylthiogalactoside. After disruption of the cells the four different glutathione-S-transferase fusion proteins were found to be soluble in aqueous solutions. Therefore, the four fusion proteins could be purified from crude bacterial lysates under non-denaturing conditions by affinity chromatography on immobilized glutathione to a purity of about 80%.

Active immunizations and protection experiments: 4 groups (A–D) of 68 female BALB/c Mice (10–12 weeks old) each received 100 µg of antigen: GST (A), GST-OprF+ GST-OprI (B), GST-OprF-OprI (C) or GST-OprI-OprF (D), suspended in 100 µl of "ABM 2 complete" as adjuvant (Sebak, Aidenbach) on day 0. Booster injections were given with an equal amount of antigen suspended in 100 µl $Al(OH)_3$ on days 14, 28 and 42. On day 49 animals were bled from the tail vein for serum collection to determine antibody titers in the pooled sera of 7–10 mice from each group. Four days later, all the animals received immunosuppressive treatment. For immunosuppression mice received three injections of 150 μg cyclosphosphamide. (Serva, Heidelberg, Germany) per g of body weight in 0.25 ml of phosphate-buffered saline (PBS) on days 53, 55, 57. On day 58, each antigen group was divided into 4 subgroups, I, II, III, IV, containing 16–17 animals per subgroup, The mice of groups A–D received introperitoneally either $5\times10^1$ (subgroup I), $5\times10^2$ (subgroup II), $5\times10^3$ (subgroup III) or $5\times10^4$ (subgroup IV) CFU of $P.$ $aeruginosa$ serogroup 1.15 additional nonimmunized mice underwent only immunosuppression without bacterial challenge. This control group was used to confirm the state of leukopenia and to exclude nonspecific infections. All surviving animals were monitored for 10 days after infection.

Expression and purification of recombinant OprF–OprI in yeast: For expression of the $P.$ $aeruginosa$ outer membrane proteins in $S.$ $cerevisiae$ the yeast/$E.$ $coli$ shuttle vector pYepsec1 (Baldari, C. et al. (1987) EMBO. J. 6, pp. 229–234) was used. This plasmid expresses polypeptides fused to the signal sequence of the Kluyveromyces lactis killer toxin. The NcoI/HindIII DNA fragment from pGEX-OprF–OprI, which codes for the OprF–QprI hybrid protein, was isolated, and cloned into pYepsec1, cut with BamHI and HindIII (yielding pYepsec1-F-I). The NcoI and BamHI sites were turned into blunt ends with Klenow enzyme before ligation, whereas the HindIII site was not treated. The soluble OprF–OprI hybrid protein expressed in yeast was purified by affinity chromatography, using a monoclonal antibody directed against epitope D1. The MAb was coupled to BrCN activated sepharose 4B (Pharmacia, Freiburg, Germany), in accordance with the instructions of the manufacturer. Yeast extracts in PBS were loaded onto the column, unspecific bound material was eluted with 0.1 M glycin pH 9.0 buffer containing 0.5 M NaCl. Elutions of OprI–OprF hybrid protein was carried out in 0.1 M glycin buffer, pH 11.0. The column was regenerated by washing with 0.1 M glycin, pH 2.5, followed by washing with PBS.

Production of specific immunoglobulins and passive immunization: Rabbits were immunized three times with 100 μg of purified recombinant OprF–OprI isolated from $S.$ $cerevisiae$ cell extracts (or with cell extracts from $S.$ $cerevisiae$ alone as controls) emulsified in incomplete Freund adjuvant on days 0, 14 and 28. On day 38, blood samples were obtained and allowed to clot overnight at 4° C. The serum was removed, centrifuged and stored at −20° C. In groups of 30 female SCID mice (18–20 g, Bomholtgard, Denmark), every animal in the group received either 0.5 ml of rabbit anti OprF–OprI serum or 0.5 ml of rabbit anti yeast serum. As an additional control, the animals in one group received 0.5 ml of normal saline. Those in one additional group were injected with 0.5 ml of rabbit serum against heat inactivated cells of serogroup 1 of $P.$ $aeruginosa$. After 3 hours, the animals of groups 1–6 were subdivided into 5 subgroups (a–e), receiving 0.5 ml of $P.$ $aeruginosa$ serogroup I suspension ($10^1$, $10^2$, $10^3$, $10^4$, $10^5$ CFU/ml suspended in mucin respectively. The surviving animals were observed for 1 week. 5 g mucin (Sigma, Taufkirchen, Germany) were suspended in 100 ml of distilled water, treated for 10 min. with an Ultra Turrax blender, passed through a sieve and autoclaved for 15 min at 120° C. Shortly before use, the solution was adjusted to pH 7.2–7.4 with sterile 1N NaOH.

EXAMPLES

Example 1

Epitope Mapping of OprF

In order to identify amino acid sequence sections of OprF representing B-cell epitopes as a rational basis for the choice of an Opr-based $P.$ $aeruginosa$ vaccine, we prepared monoclonal antibodies against a recombinant protein representing amino acids 58 to 350 of OprF. Binding of the MAbs was analyzed with a series of recombinant subfragments of OprF expressed in $E.$ $coli$. The MAbs discriminated between 5 different regions: aa 190–213 (D1), aa 212–240 (D2, SEE 1), aa 239–250 (D3), aa 284–316 (D4) and aa 332–350 (D5, SEE 4). The C-terminal part of OprF between aa 190 and aa 350 seemed therefore to cover most of the B cell epitopes of OprF. To further analyze the epitopes, synthetic peptides related to the above defined amino acid sections were prepared and conjugated to KLH. Polyclonal antisera against these peptides were raised in rabbits. Table 1 shows that peptides D1–D5 were recognized by the corresponding polyclonal antisera. The peptides D1, D2, D4 and D5 reacted with monoclonal antibodies, and peptides D2, D3, D4 and D5 were also recognized by polyclonal antibodies raised against recombinant OprF, thus confirming that these 5 epitopes are B-cell derived. Antisera raised against D3, D4 and, D5 recognized OprF in Western blot analysis, but viable $P.$ $aeruginosa$ cells showed positive fluorescence only after incubations with the antisera raised against D2 and D5. These two epitopes therefore seem to be surface-exposed. Additional MAbs were identified which did not react with any of the synthetic peptides, but recognized GST–OprF and further recombinant subfragments, leading to two additional epitopes, D6 and D7, which correspond to amino acid residues 240–316 and 190–250 respectively. Therefore, the region from amino acid 190 to amino acid 350 of OprF was considered to include important antigenic regions, and we decided to ascertain whether recombinant proteins carrying these epitopes are able to confer protection in animal models.

Example 2

Epitope Mapping of OprI

With the MAbs 2A1, 6A4 and 5B4 raised against native OprI, two different epitopes have been characterized (Finke, M. et al. (1991), Infect. Immun. 59, pp. 1251–1254). MAb 2A1, which had shown protective ability against $P.$ $aeruginosa$ infection, recognized the N-terminal located epitope. Subsequent studies showed that 2A1 only binds if the entire amino acid sequence from amino acid 21 to amino acid 83 is expressed. For the construction of recombinant OprI antigens as means of a subunit vaccine, the complete amino acid region 21–83 was therefore considered to be the most adequate antigen.

Example 3

Expression of Oprs in $E.$ $coli$

Figure 1:
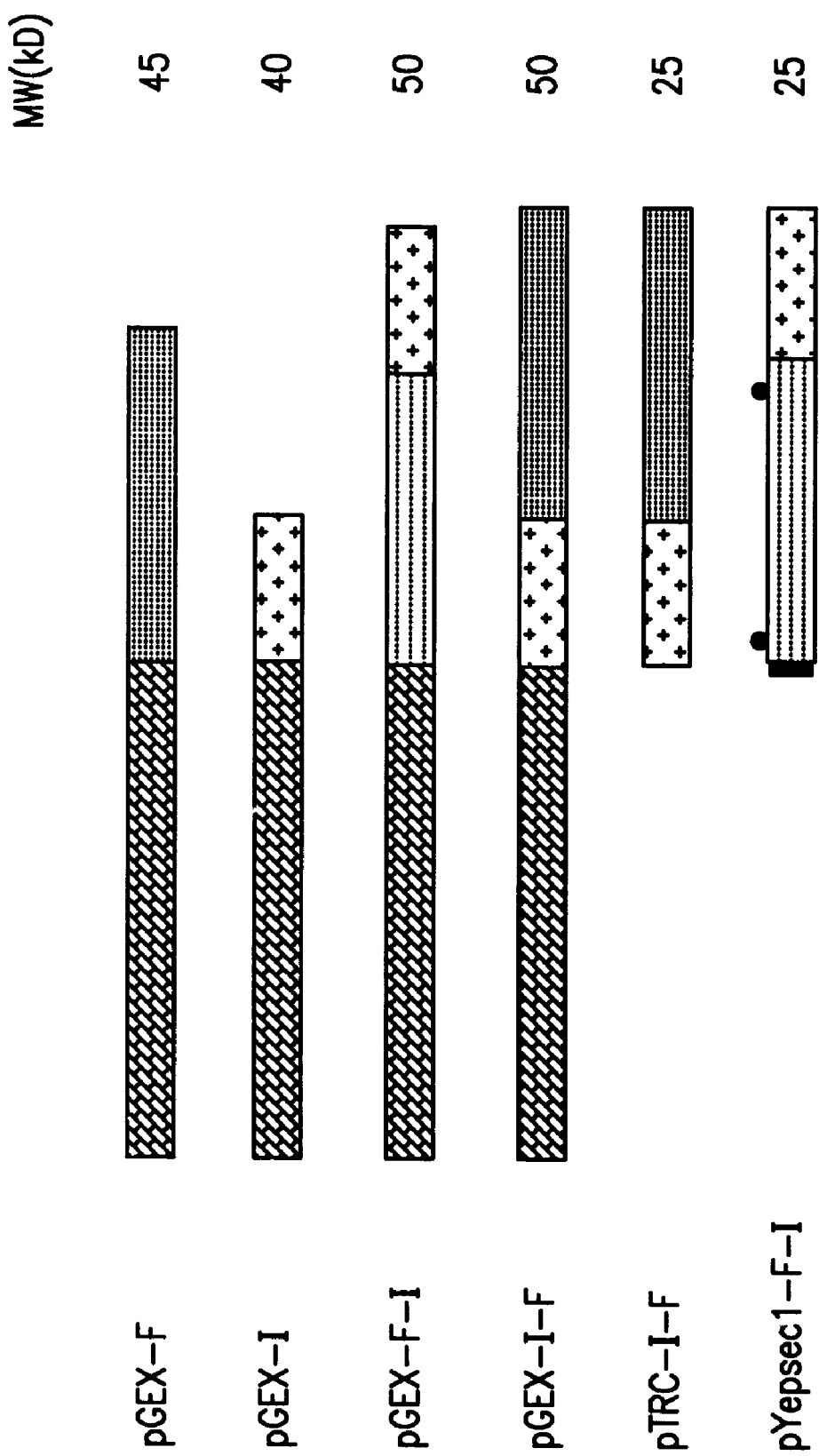
FIG. 1 is a schematic overview of the constructed recombinant fusion proteins of outer membrane proteins of *P. aeruginosa*. For expression in *E. coli* K12, the vector pGEX-2a, which codes for glutathion-S-transferase was used.

The efficacy of a single outer membrane protein of $P.$ $aeruginosa$ in a vaccine against $P.$ $aeruginosa$ infection might be improved by coexpression of the fused epitopes of two different Oprs. Four different glutathion-S-transferase-fusion proteins were expressed in $E.$ $coli$ in large amounts: GST–OprF$_{(aa\ 190\text{-}350)}$, GST–OprI$_{(aa\ 21\text{-}83)}$, GST–OprF$_{(aa\ 190\text{-}342)}$–OprI$_{(aa\ 21\text{-}83)}$ and GST–OprI$_{(aa\ 21\text{-}83)}$–OprF$_{(aa\ 190\text{-}350)}$ (FIG. 1). The recombinant proteins could be about 80% purified by affinity chromatography on immobilized glutathion. Western blot analysis of the four recombinant products with the OprI specific MAbs 6A4 and 2A1 and different OprF specific MAbs directed against the epitopes D1, D2, D4, D5, D5, D6 and D7 showed that the MAb specific epitopes were expressed by the recombinant fusion proteins.

Example 4

Active Immunization with E. coli Derived Fusion Proteins

Mice were immunized four times at two week intervals with 100 μg of recombinant GST linked fusion protein, or GST only, suspended in adjuvant "ABM complete". The antibody titers, each from the pooled sera of 8–10 mice, were analyzed by ELISA as well by Western blotting for binding activity against P. aeruginosa, and by ELISA against peptides D1–D5.

FIG. 2 shows that specific antibody titers against P. aeruginosa were obtained in all immunized groups up to serum dilutions 1:15625. Western blot analysis of the sera with P. aeruginosa polypeptides showed specific staining of OprI as well as of OprF by sera from all immunized groups. No staining of OprI or OprF was observed in the GST immunized control group. Further analysis of the sera against peptides D1–D5 (FIG. 3) showed that, in GST–OprF–OprI as well as GST–OprI–OprF immunized animals, peptides D5 and D4. predominated. In order to test whether the induced antibodies against outer membrane fusion proteins protect mice against P. aeruginosa infection, mice received three doses of cyclophosphamide for immunosuppression. Leukocyte counts determined in peripheral blood samples of 15 non-immunized control animals dropped to mean levels below 400/μl. One day later, the animals were challenged with either $5 \times 10^1$, $5 \times 10^2$, $5 \times 10^3$ or $5 \times 10^4$ CFU of P. aeruginosa serogroup 1. Survival of the animals was registered for one week. FIG. 4 and Table 2 show the survival rates of the animals after 4 different challenge doses and the $LD_{50}$ values for each of the vaccines, calculated by probit regression analysis. For groups immunized with GST only or with GST–OprI–OprF, $LD_{50}$ values as low as 1.58 and 2.65 were calculated. Simultaneous vaccination with a mixture of GST–OprI and GST–OprF induced an increase of the $LD_{50}$ value to 83.3 CFU. This difference, however, was found to be not statistically significant. In contrast, after vaccination with the hybrid GST–OprF–OprI a highly significant shift of the $LD_{50}$ value towards 1540 CFU was calculated ($p \leq 0.00$). Compared to the GST immunized controls, a protection value of 962 was calculated for the GST–OprF–OprI group. These results could be confirmed ($p \leq 0.001$) in an identically designed second experiment.

Analysis of the data by the proportional hazard model and calculation of the reduction of the rise ratios induced by the different vaccine preparations is shown in Table 2. Vaccination with GST–OprF–OprI reduced the risc ratio highly significantly ($p \leq 0.0001$) to a value of 0.3 compared to the GST immunized controls. Even for a challenge dose of $5 \times 10^3$ CFU, a significant ($p \leq 0.0019$) reduction of the risc ratio to a value of 0.69 was calculated by backward elimination for the GST–OprF–OprI vaccinated group, with reference based on GST, GST–OprF+GST–OprI, GST–OprI–OprF immunized groups, and doses one and two ($5 \times 10^1$ and $5 \times 10^2$).

Example 5

Expression of OprF–OprI in Yeast

For the expression of the OprF–OprI hybrid pro protein without an additional fusion component we chose as an alternative host cell Saccharomyces cerevisiae and as plasmid pYepsec1. OprF–OprI contained in pYepsec1-F-I (FIG. 1) was expressed only in minute amounts in S. cerevisiae. Since OprF as well as OprI are exported in Pseudomonadaceae through the periplasmic space, we tried to copy the export in S. cerevisiae. To this end, the OprF–OprI hybrid protein was fused to the secretion signal sequence of the killer toxin (kt) of the yeast Kluyveromyces lactis. The tripartite hybrid protein kt. OprF–OprI encoded by pYepsec1-F-I (FIG. 1) now consists of the following polypeptide stretches: first there are the 16 amino acids of the yeast secretion signal sequences, followed by 9 amino acids encoded by a DNA linker and then followed by the OprF specific polypeptide stretch from amino acids 190–342 and an OprI peptide including amino acids 21–83. The OprF specific polypeptide carries the potential glycosylation site asparagine-x-threonine (see FIG. 1) twice. These glycosylation sites should be recognizable if the fusion protein enters the secretionary pathway. Upon fusion to the killer toxin leader sequence, OprF–OprI was detected in yeast cell extracts by Western blot analysis, when expressed under induced condition of the $UAS_{GAL}/CYC1$ promoter; but no secreted antigen was detected in the culture broth.

The OprF–OprI fusions protein expressed in yeast did not migrate as a sharp band in SDS polyacrylamide gels, but showed a heterogeneous distribution, appearing in several smearing bands. This indicates posttranslational modification by N-glycosylation. Incubation of the recombinant P. aeruginosa antigen with endoglycosidase F resulted in the appearance of a sharp band of lower molecular weight, indicating the entering of OprF—OprI into the secretionary pathway when fused to the killer toxin leader sequence, and the glycosylation of at least one of the two potential glycosylation sites.

Example 6

Passive Immunization with Antibodies Against Yeast-derived OprF–OprI

The recombinant Pseudomonas antigen was enriched from the supernatants of yeast cell extracts by ammonium salt precipitation and immunoaffinity chromatography, using an anti OprF mouse monoclonal antibody directed against epitope D1. Rabbits were then immunized three times with the antigen, and sera were collected from the animals. Whereas the preimmune sera did not show any reactivity with either P. aeruginosa OprF or OprI, the sera from the immunized rabbits reacted specifically with the outer membrane proteins OprF and OprI from the three different ATCC strains of P. aeruginosa, as well with the three different clinical isolates of P. aeruginosa tested. The protective efficacy of these sera was tested in SCID mice for defence against a lethal challenge with P. aeruginosa. As shown in Table 3 mice injected with the control anti-yeast serum were not protected against infection even at a challenge dose of $5 \times 10^1$ (Table 3, group 1). On the other hand, mice which received the OprF–OprI specific rabbit serum were fully protected against a $5 \times 10^2$ CFU challenge dose of P. aeruginosa (Table 3, group 3), and 40% survival was observed after challenge with $5 \times 10^3$ CFU. As an additional control, protection by rabbit serum induced against LPS of the challenge strain, P. aeruginosa serogroup 1, was tested. Up to a challenge dose of $5 \times 10^3$, 100% of the animals protected with LPS specific serum survived (Table 3, group 5). No survival couold be observed in this group after a 10-fold higher challenge dise of $5 \times 10^4$. Statistical analysis was used to compare the protective doses of OprF–OprI specific serum, of LPS specific serum and the anti-yeast control group for protection against P. aeruginosa infection The results showed an 85-fold increase in potency of the OprF–OprI serum in comparison with the antiyeast serum ($p \leq 0.002$—see Table 3, group 3). As against this, a 325 higher potency was calculated for the LPS specific serum than for the anti-yeast serum ($p \leq 0.001$).

TABLE 1

Characterization of B cell-epitopes of P. aeruginosa OprF

| peptide | OprF specific aa region | MAbs* | rabbit anti OprF ELISA (against peptide) | rabbit antisera** ELISA (against peptide) | rabbit antisera** Western blot (against OprF) | rabbit antisera** immunofluorescence of intact P. aeruginosa*** |
|---|---|---|---|---|---|---|
| D1 | 190–213 | + | – | + | – | – |
| D2 | 212–240 | + | + | + | – | + |
| D3 | 239–250 | – | + | + | + | – |
| D4 | 284–216 | + | + | + | + | – |
| D5 | 332–350 | + | + | + | + | + |

*MAbs were induced in mice against a recombinant protein representing amino acids 58–350 of OprF, binding to peptides D1–D5 was analyzed by ELISA.
**Rabbits were immunized with peptides linked to KLH.
***estimated with P. aeruginosa serogroup 11 (ATCC 33359).

TABLE 2

Statistical analysis of survival of mice*

| | Vaccine | | | |
|---|---|---|---|---|
| | GST | GST-OprF + GST-OprI | GST-OprF-OprI | GST-OprI-OprF |
| $LD_{50}$ | 1.58 | 83.34 | 1540++ | 2.65 |
| Shift $LD_{50}$** | 1 | 52 | 962 | 1.7 |
| Risk Ratio*** | 1 | 0.732 | 0.344+++ | 0.889 |

*mice were vaccinated with the indicated GST linked recombinant Oprs or GST as control.
**$LD_{50}$ values were calculated by probit analysis (Finney, D. J. (1971), Probit analysis, Cambridge University Press, Cambridge).
++$P < 0,05$ versus GST group.
+++$P < 0.0001$ versus GST group.
*** Risk ratios were calculated by the proportional hazard model (Lawless, J. F. (1982), Statistical Methods for Lifetime Data, John Wiley & Sons, New York) with reference based on GST group.

TABLE 3

Protection against P. aeruginosa infection in SCID mice by rabbit anti OprF-OprI sera Surviving animals after transfer of specific rabbit serum before challenge, group no. (n = 5)

| challenge dose** (CFU) | 1 yeast* control | 2 yeast* control 1:10 | 3 OprF-OprI* | 4 OprF-OprI* 1:10 | 5 P. aeruginosa*** | 6 chalenge control | 7 mucin control |
|---|---|---|---|---|---|---|---|
| $5 \times 10^0$ | 5 | 5 | 5 | 5 | 5 | 1 | |
| $5 \times 10^1$ | 1 | 1 | 5 | 4 | 5 | 0 | |
| $5 \times 10^2$ | 1 | 0 | 5 | 2 | 5 | 0 | |
| $5 \times 10^3$ | 0 | 1 | 2 | 0 | 5 | 0 | |
| $5 \times 10^4$ | 0 | 0 | 0 | 0 | 0 | 0 | |
| mucin | | | | | | | 5 |

*Rabbit serum of animals immunized with the indicated antigen.
**Female C.B-17 scid/scid mice (SCID) were challenged intraperitoneally with the indicated colony forming units (CFU) of P. aeruginosa serogroup 1 suspended with 0.5 ml of mucin.
***rabbit serum of animals immunized with P. aeruginosa serogroup 1. Statistical analysis (probit analysis for parallel line model); group 1 versus group 3: 85-fold increase in potency, significance (chi-square), 0.002. Group 1 versus group 5; 325-fold increase in potency, significance 0.001

What is claimed is:

1. A nucleic acid molecule coding for a hybrid protein comprising a first polynucleotide encoding the polypeptide of SEQ ID NO:9 of a *Pseudomonas aeruginosa* outer membrane protein I (OprI) and a second polynucleotide encoding the polypeptide of SEQ ID NO:11 of a *Pseudomonas aeruginosa* outer membrane protein F (OprF), wherein the OprI polynucleotide is fused with its amino terminal end to the carboxy terminal end of a carboxy terminal portion of the OprF polynucletide.

2. The nucleic acid molecule of claim 1, wherein the second polynucleotide encodes the polpeptide of amino acid residues 1–153 of SEQ ID NO:11.

3. A nucleic acid molecule coding for a hybrid protein comprising a *Pseudomonas aeruginosa* outer membrane protein I which is fused with its amino terminal end to the carboxy terminal end of a carboxy terminal portion of a *Pseudomonas aeruginosa* outer membrane protein F, said carboxy terminal portion comprising at least one surface-exposed B-cell epitope selected from the group consisting of amino acid residues 23 through 51, inclusive, of SEQ ID NO:11 (SEE 1), amino acid residues 54 through 67, inclusive, of SEQ ID NO:11 (SEE 2), amino acid residues 96 to 109, inclusive, of SEQ ID NO:11 (SEE 3) and amino acid residues 143 through 161, inclusive of SEQ ID NO:11 (SEE 4).

4. A recombinant vector comprising the nucleic acid molecule of claim 1, and a promoter operably linked to said nucleic acid molecule, whereby said hybrid protein can be expressed in a host cell.

5. A recombinant vector comprising the nucleic acid molecule of claim 2, and a promoter operably linked to said nucleic acid molecule, whereby said hybrid protein can be expressed in a host cell.

6. A recombinant vector comprising the nucleic acid molecule of claim 3, and a promoter operably linked to said nucleic acid molecule, whereby said hybrid protein can be expressed in a host cell.

7. A host cell transformed with the recombinant vector of claim 4.

8. A host cell transformed with the recombinant vector of claim 5.

9. A host cell transformed with the recombinant vector of claim 6.

* * * * *